(12) United States Patent
Radina et al.

(10) Patent No.: US 9,844,482 B2
(45) Date of Patent: Dec. 19, 2017

(54) MEDICAL HEAD HOLDER

(75) Inventors: Christian Radina, Garching (DE); Rupert Heigl, Markt Schwaben (DE); Markus Graedler, Erlangen (DE)

(73) Assignee: Brainlab AG, Munich (DE)

( * ) Notice: Subject to any disclaimer, the term of this patent is extended or adjusted under 35 U.S.C. 154(b) by 516 days.

(21) Appl. No.: 14/379,783

(22) PCT Filed: Mar. 1, 2012

(86) PCT No.: PCT/EP2012/053495
§ 371 (c)(1),
(2), (4) Date: Aug. 20, 2014

(87) PCT Pub. No.: WO2013/127457
PCT Pub. Date: Sep. 6, 2013

(65) Prior Publication Data
US 2015/0020817 A1    Jan. 22, 2015

(51) Int. Cl.
*A61G 13/12*  (2006.01)
*A61B 90/14*  (2016.01)
*A61B 90/00*  (2016.01)

(52) U.S. Cl.
CPC .......... *A61G 13/121* (2013.01); *A61B 90/14* (2016.02); *A61G 13/129* (2013.01); *A61G 13/1295* (2013.01); *A61B 2090/065* (2016.02)

(58) Field of Classification Search
CPC ................................................. A61G 13/121
USPC ....... 606/53–54, 59, 130; 600/424–429, 207, 600/411, 417; 403/59, 83, 86; 5/637,
(Continued)

(56) References Cited

U.S. PATENT DOCUMENTS 2,966,383 A    12/1960 Boetcker et al.
3,835,861 A    9/1974  Kees, Jr. et al.
4,169,478 A    10/1979 Hickmann
(Continued)

FOREIGN PATENT DOCUMENTS

DE    197 18 536    11/1998
DE    198 41 250    2/2000
(Continued)

OTHER PUBLICATIONS

International Search Report and Written Opinion for International Application No. PCT/EP2012/053495 dated Dec. 13, 2012.

*Primary Examiner* — Tarla Patel
(74) *Attorney, Agent, or Firm* — Tucker Ellis LLP

(57) ABSTRACT

A medical head holder includes at least two opposing engagement members configured to engage the head of a patient, a frame, connector and coupling members, and a force applicator. The frame includes first and second frame sections which are displaceably coupled with each other, wherein each frame section supports at least one of the engagement members. The connecting member guides the first and second frame sections for displacement relative to each other, and selectively detachably fixes the frame sections with each other. The coupling member is selectively fixed to the second frame section and displaceably couples the second engagement member with the second frame section. The force applicator is detachably coupled to the second frame section and acts on the coupling member so as to cause the second engagement member to be displaced and/or fixed relative to the second frame section.

15 Claims, 2 Drawing Sheets

(58) Field of Classification Search
USPC ....... 5/622, 640, 643; 378/204–205; 602/32, 602/36, 39, 18; 128/869, 845–846
See application file for complete search history.

(56) References Cited

U.S. PATENT DOCUMENTS

| | | | |
|---|---|---|---|
| 4,545,572 A | 10/1985 | Day | |
| 5,254,079 A | 10/1993 | Agbodoe et al. | |
| 5,269,034 A * | 12/1993 | Day | A61B 90/14 403/59 |
| 5,276,927 A * | 1/1994 | Day | A61G 13/121 5/601 |
| 5,537,704 A | 7/1996 | Dinkler | |
| 5,560,728 A | 10/1996 | McFadden | |
| 6,179,846 B1 | 1/2001 | McFadden | |
| 6,315,783 B1 | 11/2001 | Katz et al. | |
| 6,355,049 B1 * | 3/2002 | Gill | A61B 90/14 5/622 |
| 7,507,244 B2 | 3/2009 | Dinkler | |
| 7,730,563 B1 | 6/2010 | Sklar et al. | |
| 2001/0052151 A1 | 12/2001 | Reinhardt et al. | |
| 2007/0250071 A1 | 10/2007 | Soerensen et al. | |
| 2008/0251086 A1 | 10/2008 | Dinkler | |

FOREIGN PATENT DOCUMENTS

| | | |
|---|---|---|
| DE | 200 15 355 | 2/2001 |
| DE | 20 2004 006 726 | 6/2004 |
| DE | 20 2006 006734 | 6/2006 |
| EP | 0 623 318 | 4/1994 |
| EP | 1 849 427 | 10/2007 |
| WO | 94/06391 | 3/1994 |
| WO | 96/02204 | 2/1996 |
| WO | 2009/014721 | 1/2009 |
| WO | 2009/149235 | 12/2009 |
| WO | 2011/088289 | 7/2011 |

* cited by examiner

MEDICAL HEAD HOLDER

RELATED APPLICATION DATA

This application is a national phase application of International Application No. PCT/EP2012/053495 filed Mar. 1, 2012 and published in the English language.

BACKGROUND

The present invention relates to a head holder for holding the head of a patient in a surgical environment.

SUMMARY

In order to prevent a patient's head from moving during surgery, the patient's head is fixed by means of a head holder comprising pins which engage the patient's skull.

The head is typically fixed in the head holder by two or three persons in a surgical environment. Although this procedure is well-established and practised, it is time-consuming and requires an experienced team in order to fix the head holder such that each pin is positioned perfectly on the patient's head. The surgeons must take into account the shape of the head, aesthetic issues and also the assessability of the planned craniotomy. These requirements often mean that the head holder has to be removed and re-positioned, as the fixing method is not perfect.

It is an object of the present invention to fix a medical head holder on a patient's head in an improved way and to overcome the fixing problems in the prior art.

The subject-matter of independent claim 1 addresses the problems in the prior art and provides a head holder for fixing a patient's head in an improved way. The dependent claims define preferred embodiments of the present invention.

BRIEF DESCRIPTION OF THE EXAMPLE EMBODIMENTS

The medical head holder according to an example embodiment of the present application comprises: at least two opposing engagement members configured to engage the head of a patient; a frame comprising a first and a second frame section which are displaceably coupled to each other, each frame section supporting at least one of the engagement members; connecting means which allow the first and second frame sections to be displaced and by means of which the first and second frame sections are guided and can be detachably fixed to each other; coupling means which are attached to the second frame section and by means of which the second engagement member is displaceably coupled to the second frame section and can be fixed to the second frame section; and a force applicator which is detachably coupled to the second frame section and acts on the coupling means so as to cause the second engagement member to be displaced and/or fixed relative to the second frame section.

In other words, the force applicator can be separated from the second frame section of the head holder and therefore also from the head holder as a whole. The force applicator does not therefore have to remain coupled to the head holder during surgery and is therefore not an encumbrance to the surgeons.

In accordance with a preferred embodiment, both displacing the first and second frame sections relative to each other and displacing the second engagement member relative to the second frame section alters the distance between the at least two opposing engagement members, wherein displacing the first and second frame sections relative to each other in particular effects a coarse adjustment and displacing the second engagement member relative to the second frame section effects a fine adjustment of the distance between the two opposing engagement members.

In other words, the distance between the opposing engagement members can be changed by moving the first and second frame sections relative to each other or by moving the second engagement member relative to the second frame section, thereby adjusting the clamping gap in which a patient's head is placed. Preferably, the first and second frame sections are moved relative to each other for a coarse adjustment of the distance between the opposing engagement members, and the second engagement member is moved relative to the second frame section for a fine adjustment of the distance between the opposing engagement members. When a patient's head is engaged by the opposing engagement members, adjusting the distance between the opposing engagement members is accompanied by an adjustment of the force which acts on the patient's head via the opposing engagement members.

In accordance with another preferred embodiment of the present invention, the second engagement member is free to rotate while being displaced, in particular about an axis which is parallel to the displacement direction of the second engagement member relative to the second frame section, wherein the coupling means are configured to block this rotational degree of freedom once the second engagement member has been displaced relative to the second frame section. The rotational degree of freedom of the second engagement member while it is being displaced relative to the second frame section enables a surgeon to alter the orientation of the head holder with respect to the patient's head if the second engagement member engages the patient's head at multiple locations. Assuming that the second engagement member is already engaging the patient's head at multiple locations, the surgeon is still able to adjust the orientation of the head holder, without also having to change the engagement locations.

The degree of freedom, in particular the rotational freedom of the second engagement member, also has to be blocked for the final placement of the head holder relative to the patient's head. Therefore, the coupling means can be configured to block the degree of freedom once the distance between the engagement members has been fine-adjusted by displacing the second engagement member relative to the second frame section.

In accordance with another preferred embodiment of the present invention, the force applicator is configured to be detached once the second engagement member has been fixed to the second frame section. Since placing the head holder on the patient's head is completed by fixing the second engagement member to the second frame section, the force applicator—which is designed to perform a fine adjustment of the distance between the opposing engagement members—becomes redundant. The force applicator is therefore preferably separated from the head holder once the second engagement member has been fixed to the second frame section, since it could be an encumbrance to the surgeons later on during surgery.

In accordance with another preferred embodiment of the present invention, the force applicator comprises gripping means which are configured to be gripped by a user in order to displace and/or fix the second engagement member. Once the first and second frame sections have been fixed to each other using the coupling means, the surgeon only has to operate the force applicator for the following procedure, i.e. performing the fine adjustment of the distance between the first and second engagement members and fixing the second engagement member relative to the second frame section. In particular, the surgeon fine-adjusts the position of the second engagement member using a first gripping means which can be a hand wheel, a lever or any other kind of suitable means known to a skilled person. The force applicator can also comprise a second gripping means which can be a second hand wheel or any other suitable means which is known to a skilled person and which the surgeon can use to fix the second engagement member to the second frame section.

The first and/or second gripping means could however also be attached to any other part of the head holder, for example the second frame section, instead of being part of the force applicator.

In accordance with another preferred embodiment of the present invention, the force applicator comprises a coupling which transmits force and/or torque from the force applicator to the coupling means and which allows the force applicator to be separated from the second frame section. In other words, the coupling serves as an interface which is able to transmit force and/or torque—which has been applied by the user to the force applicator, for example using the gripping means—to the coupling means, wherein the force and/or the torque is used to displace the second engagement member relative to the second frame section and/or to fix the second engagement member to the second frame section by the coupling means. Once the second engagement member has been displaced properly and fixed to the second frame section, the force applicator can be detached from the second frame section using the coupling as an interface.

In accordance with another preferred embodiment of the present invention, the force applicator comprises a force indicator which indicates the force acting on the patient's head via the engagement members. As already described further above, a certain force is applied to a patient's head which is arranged between and engaged by the opposing engagement members. As soon as the distance between the engagement members decreases, the force acting on the patient's head via the engagement members increases. However, a force indicator is provided in order to provide the surgeon with information about the force currently being applied to the patient's head and so prevent the surgeon from applying too much force to the patient's head by decreasing the distance between the opposing engagement members by too much and also prevent the surgeon from applying a force to the patient's head which is insufficient to properly fix the patient's head by means of the head holder. In accordance with another preferred embodiment, the connecting means comprise a translational guide, and the first and second frame sections are displaced relative to each other in a translational movement.

Although the first and second frame sections could for example be displaced relative to each other in a rotational movement about a pivot axis, it is preferred if the first and second frame sections and therefore also the first and second engagement members are displaced relative to each other in a translational movement for which a translational guide is provided as part of the connecting means. The translational guide could be a hollow guide which is formed on the first or second frame section in order to encompass a corresponding bar formed on the second or first frame section, respectively, so as to allow a translational movement of the first and second frame sections relative to each other. The translational guide could also be configured to allow a translational movement only, wherein all other degrees of freedom are blocked. In the embodiment comprising a hollow guide encompassing a corresponding bar, the hollow guide and the bar could have cross-section which prevents a rotational movement perpendicular to the permitted translational movement, such as for example a trapeziform cross-section.

In accordance with another preferred embodiment of the present invention, the connecting means comprises a form-fit fastener, in particular a first toothed member which is assigned to the first frame section and a second toothed member which is assigned to the second frame section, wherein the first and second toothed members are configured to engage each other, thereby preventing a relative movement of the frame sections. In other words, the first and second frame sections are fixed to each other in a form fit, wherein the first frame section comprises a first toothed member and the second frame section comprises a second toothed member which prevent a movement, in particular a translational movement, of the frame sections relative to each other. At least one of the toothed members can in particular be a toothed bar. The teeth of the respective toothed members also have mutually co-operating shapes, so as to allow the first and second toothed members to engage. The teeth of each toothed member can for example have a symmetrical or asymmetrical shape, such as for example a serrated shape.

In accordance with another preferred embodiment of the present invention, at least one of the toothed members is coupled to a corresponding frame section—in particular, the second toothed member is coupled to the second frame section—via a resilient coupling which allows the toothed member to move relative to the corresponding frame section, specifically in a direction perpendicular to the relative movement direction of the frame sections. Allowing a toothed member to move relative to a corresponding frame section by means of a resilient coupling enables the first and second frame sections to be displaced, since the teeth of the respective toothed members are allowed to slide over each other without losing contact while the first and second frame sections are displaced, specifically in a translational guide which only allows a translational movement of the first and second frame sections relative to each other.

In accordance with another preferred embodiment of the present invention, at least one of the following settings is possible for the resilient coupling: toothed members out of engagement, relative movement of the frame sections possible in both directions; engagement of toothed members caused solely by a resilient force of the resilient coupling acting on one of the toothed members, relative movement of the frame sections possible in one direction only, preferably in a direction which reduces the distance between the two opposing engagement members; engagement of toothed members caused by a fixing mechanism, no relative movement of the frame sections possible, wherein said settings are in particular selected by means of a lever of the fixing mechanism, which can assume different positions in accordance with the different settings and which acts on the resilient coupling.

In other words, different settings of the resilient coupling are possible. The first setting, in which the toothed members are out of engagement and do not contact each other, allows the first and second frame sections to be displaced in accordance with the degree of freedom which is allowed by the connecting means, in particular by the translational guide of the connecting means. When a translational guide is provided and the toothed members are out of engagement, the first and second frame sections can be displaced in both directions along the translational guide.

Another setting allows the first and second frame sections to be displaced in one direction only, along the translational guide if provided. The teeth of both the toothed members have a serrated shape, such that the flat sides of the teeth of the respective toothed members can slide over each other, whereas the steep sides of the teeth of the respective toothed members prevent the toothed members from sliding over each other. Although the toothed members engage each other, the resilient coupling allows a toothed member to move relative to its corresponding frame section and so also allows the teeth to slide over each other via their flat sides.

A third setting does not allow the first and second frame sections to be displaced, wherein a fixing mechanism can be provided which presses the toothed members onto each other, such that the resilient coupling cannot allow a toothed member to move relative to its corresponding frame section.

A lever, in particular an eccentric lever, can be provided which can assume different positions in accordance with the above settings and which acts on the resilient coupling, for example via the toothed member. The surgeon can select one of the above settings by positioning the lever accordingly.

In accordance with another preferred embodiment of the present invention, substantially all of the elements of the head holder are made of a radiolucent material, in particular carbon fibre laminate, carbon fibre reinforced polyether ether ketone (PEEK™) and/or polyether ketone. Metal and/or ceramic parts do not or at least substantially do not form part of the medical head holder or are at least detachable from the head holder. By manufacturing the medical head holder from radiolucent material, it is possible to avoid artefacts caused by the head holder when generating CT images. Substantially all of the elements of the head holder can be made of the same radiolucent material or of different radiolucent materials. The first and second frame sections are preferably made of carbon fibre laminate, with carbon fibre reinforced PEEK™ attachments.

In accordance with another preferred embodiment of the present invention, substantially all of the radio-opaque elements, in particular all of the radio-opaque elements of the head holder, are configured to be detached from the head holder, specifically once the first and second frame sections and the second engagement member have been fixed to each other. Since the force applicator is configured to be detached from the head holder, it does not therefore matter if certain components of the force applicator are made of a radio-opaque material.

In accordance with another preferred embodiment of the present invention, the medical head holder comprises an alignment aid which extends between the first and second frame sections and is in particular configured to be detached from the head holder, specifically once the first and second frame sections and the second engagement member have been fixed to each other. Such an alignment aid can for example be formed by a textile strap or a thin plastic film, which can also comprise at least one adhesive section for fixing the alignment aid. If the head holder comprises L-shaped frame sections connected to each other via one of their arms so as to form a substantially U-shaped head holder, then the alignment aid can be attached to the remaining ends of the frame sections so as to form a circumferential head holder. Since positioning the head holder on the patient's head typically involves a proper adjustment of the centreline of the head holder with respect to the centre of the head, after which the surgeon looks for suitable entry points for the engagement members, an alignment aid which extends between the first and second frame sections helps in positioning the head holder.

In accordance with another preferred embodiment of the present invention, the length of the alignment aid is adjustable and/or the alignment aid is a flexible strap. An alignment aid which is attached to both frame sections bears the weight of the head holder while the head holder is being aligned, such that the surgeon or any other person does not have to carry the head holder.

A head holder is also disclosed which comprises the features as described above but in which the force applicator is not detachably coupled to the second frame section but can rather be permanently fixed to the frame section, as in the examples that follow below.

A medical head holder in accordance with an example embodiment includes at least two opposing engagement members configured to engage the head of a patient; a frame comprising a first and a second frame section which are displaceably coupled to each other, each frame section supporting at least one of the engagement members; connecting means which allow the first and second frame sections to be displaced and by means of which the first and second frame sections are guided and can be detachably fixed to each other; coupling means which are attached to the second frame section and by means of which the second engagement member is displaceably coupled to the second frame section and can be fixed to the second frame section; and a force applicator which acts on the coupling means so as to cause the second engagement member to be displaced and/or fixed relative to the second frame section.

In an example embodiment—both displacing the first and second frame sections relative to each other and displacing the second engagement member relative to the second frame section alters the distance between the at least two opposing engagement members, wherein displacing the first and second frame sections relative to each other in particular effects a coarse adjustment and displacing the second engagement member relative to the second frame section effects a fine adjustment of the distance between the two opposing engagement members.

In an example embodiment, the second engagement member is free to rotate while being displaced, in particular about an axis which is parallel to the displacement direction, and wherein the coupling means are configured to block this rotational degree of freedom once the second engagement member has been displaced.

In an example embodiment, the force applicator comprises gripping means which are configured to be gripped by a user in order to displace and/or fix the second engagement member.

In an example embodiment, the force applicator comprises a force indicator which indicates the force acting on the patient's head via the engagement members.

In an example embodiment, the connecting means comprise a translational guide, and the first and second frame sections are displaced relative to each other in a translational movement.

In an example embodiment, the connecting means comprise a form-fit fastener, in particular a first toothed member which is assigned to the first frame section and a second toothed member which is assigned to the second frame section, wherein the first and second toothed members are configured to engage each other, thereby preventing a relative movement of the frame sections.

In an example embodiment, at least one of the toothed members is coupled to a corresponding frame section—in particular, the second toothed member is coupled to the second frame section—via a resilient coupling which allows the toothed member to move relative to the corresponding frame section, specifically in a direction perpendicular to the relative movement direction of the frame sections.

In an example embodiment, at least one of the following settings is possible for the resilient coupling: toothed members out of engagement, relative movement of the frame sections possible in both directions; engagement of toothed members caused solely by a resilient force of the resilient coupling acting on one of the toothed members, relative movement of the frame sections possible in one direction only, preferably in a direction which reduces the distance between the two opposing engagement members; engagement of toothed members caused by a fixing mechanism, no relative movement of the frame sections possible, wherein said settings are in particular selected by means of a lever of the fixing mechanism, which can assume different positions in accordance with the different settings and which acts on the resilient coupling.

In an example embodiment, substantially all of the elements of the head holder are made of a radiolucent material, in particular carbon fibre laminate, carbon fibre reinforced PEEK™ and/or polyether ketone.

In an example embodiment, substantially all of the radio-opaque elements, in particular all of the radio-opaque elements of the head holder, are configured to be detached from the head holder, specifically once the first and second frame sections and the second engagement member have been fixed to each other.

An example embodiment further includes an alignment aid which extends between the first and second frame sections and is in particular configured to be detached from the head holder, specifically once the first and second frame sections and the second engagement member have been fixed to each other.

In an example embodiment, the length of the alignment aid is adjustable and/or the alignment aid is a flexible strap.

BRIEF DESCRIPTION OF THE FIGURES

The example embodiments of the present invention shall now be described on the basis of preferred embodiments which are shown in the enclosed figures. The invention can comprise any of the features described herein, alone or in any expedient combination.

DETAILED DESCRIPTION

Figure 1:
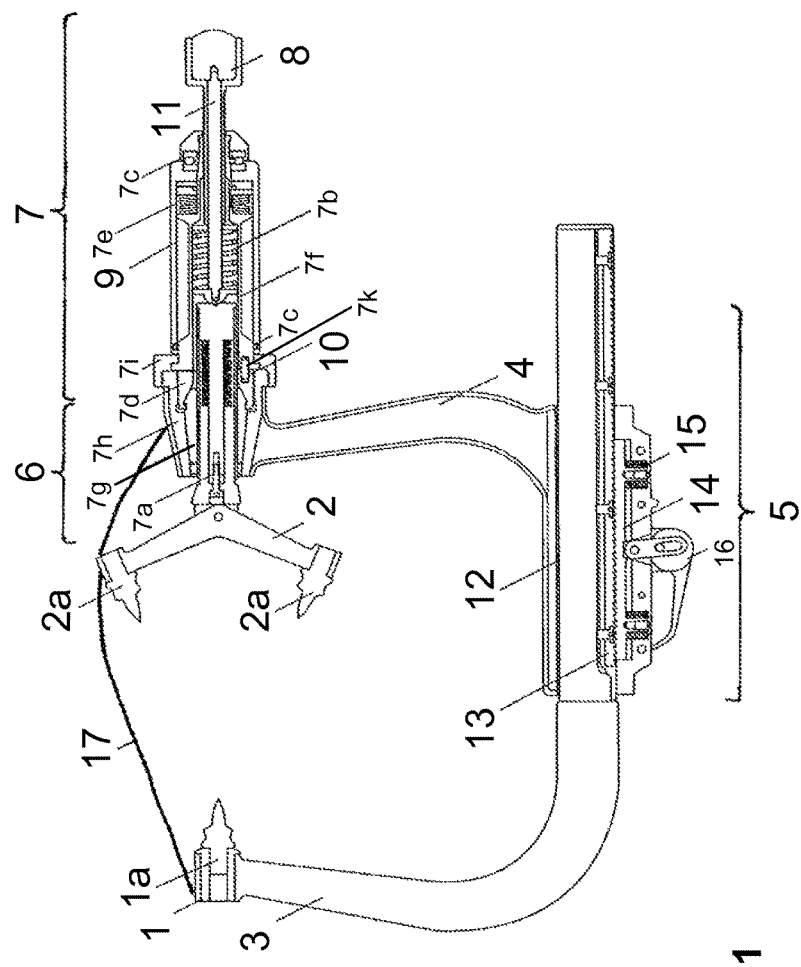
FIG. 1 shows a first embodiment of the head holder in accordance with the invention.

FIG. 1 shows a medical head holder, comprising a first substantially L-shaped frame section 3 and a second substantially L-shaped frame section 4, which are connected to each other via connecting means 5. A first engagement member 1 comprising one head pin 1a is attached to the free end of the first frame section 3, and a second engagement member 2 comprising two head pins 2a is attached to the free end of the second frame section 4.

The connecting means 5 comprise a trapeziform translational guide 12 which allows a translational movement of the first frame section 3 relative to the second frame section 4. The second frame section 4 encompasses the first frame section 3, thereby forming the translational guide 12. The first frame section 3 comprises a first toothed member 13 which is rigidly attached to the first frame section 3. The second frame section 4 comprises a toothed member 14 which is resiliently coupled to the second frame section 4 via the resilient coupling 15 formed by two sets of disc springs. The resilient coupling 15 allows the second toothed member 14 to move relative to the second frame section 4 in a direction which is perpendicular to the translational movement of the first and second frame sections 3, 4 relative to each other. The connecting means 5 also comprise an eccentric lever 16 which can assume three positions, namely a closed) (0° position as shown in FIG. 1, a half-open (90°) position and a fully open (180°) position. In the closed position, the eccentric lever 16 presses the second toothed member 14 against the first toothed member 13 such that the toothed members 13 and 14 engage each other, and the second toothed member 14 cannot be moved relative to the second frame section 4. In the half-open position, the lever 16 does not apply any force to the second toothed member 14, hence the only force pressing the second toothed member 14 against the first toothed member 13 is applied by the two sets of disc springs forming the resilient coupling 15. Since the teeth of the toothed members 13 and 14 have a serrated shape and the second toothed member 14 can move downwards in FIG. 1, against the spring force, the first and second frame sections 3, 4 can be moved relative to each other in a direction which "closes" the head holder and moves the engagement members 1 and 2 together with their respective head pins 1a and 2a towards each other, so as to engage a patient's head.

In its fully open (180°) position, the lever 16 pulls the second toothed member 14 away from the first toothed member 13, against the spring force of the two sets of disc springs, such that the toothed members 13 and 14 are out of engagement, and the engagement members 1 and 2 on the frame sections 3 and 4 can be moved towards or away from each other.

The second frame section 4 also comprises coupling means 6 which displaceably couple the second engagement member 2 to the second frame section 4 and which also fix the second engagement member 2 to the second frame section 4. The second frame section 4 also comprises a force applicator 7 which acts on the coupling means 6 so as to cause the second engagement member 2 to be displaced and fixed relative to the second frame section 4. The force applicator 7 also comprises a first gripping means 8, a second gripping means 9, a coupling 10 and a force indicator 11. A surgeon can grip and rotate the gripping means 8, wherein the thread on the gripping means 8 generates a translational movement of the gripping means 8 to the left or right in FIG. 1. Moving the gripping means 8 to the left also causes the cylinder 7a—which can be a polygonal cylinder and can be freely rotated and translated relative to the second frame section 4—to move to the left, since the gripping means 8 acts translationally on the cylinder 7a via the spring 7b. The cylinder 7a is in turn connected to the second engagement member 2. The surgeon therefore moves the second engagement member 2 as far as is necessary to the left, towards the first engagement member 1, using the gripping means 8.

The cylinder 7a acts on the force indicator 11 and pushes it to the right, against the spring force generated by the spring 7b. As the force indicator 11 is pushed to the right, it protrudes out of the right-hand end of the first gripping means 8, thereby indicating to the surgeon the force which is being applied to the patient's head via the engagement members 1 and 2. If the force is too high, the surgeon can move the gripping means 8 to the right, thereby also moving the cylinder 7a and the engagement member 2 to the right and so decreasing the force acting on the patient's head.

Once the distance between the second engagement member 2 and the first engagement member 1—and therefore the force being applied to the patient's head—has been properly adjusted, the surgeon can then grip and turn the second gripping means 9 in order to fix the second engagement member 2 to the second frame section 4. Bearings 7c allow the second gripping means 9 to be rotated relative to the first gripping means 8. The second gripping means 9 is coupled to the threaded sleeve 7d via the frictional coupling 7e and the rotational element 7f, wherein the frictional coupling 7e limits the torque which is applied to the threaded sleeve 7d. The rotational element 7f and the threaded sleeve 7d are coupled via one or more pins 10 only, such that it is possible to detach the force applicator 7 from the head holder. The one or more pins 10 can be directly attached to the rotational element 7f or to the threaded sleeve 7d. It is also conceivable for a first group of pins 10 to be directly coupled or attached to the rotational element 7f and a second group of pins 10 to be directly coupled or attached to the threaded sleeve 7d.

Alternatively, the one or more pins 10 can be resiliently coupled to the rotational element 7f or to the threaded sleeve 7d, for example by means of springs, in particular coil springs 7k. This allows the force applicator 7 to be attached to the coupling means 6 by screwing the box nut 7i onto the base element 7h without the need for pins 10 to engage corresponding bores in the rotational element 7f or the threaded sleeve 7d, respectively. By turning the gripping means 9, the pins 10 are forced into corresponding bores as soon as the bores are aligned with the pins 10.

Turning the second gripping means 9 also causes the rotational element 7f and—by means of the pins 10 which engage the threaded sleeve 7d and the rotational element 7f—the threaded sleeve 7d to turn. The threaded sleeve 7d is coupled to a tapered element 7g which is slotted and can freely rotate relative to the threaded sleeve 7d. The threaded sleeve 7d engages a tapered base element 7h via a thread, such that turning the threaded sleeve 7d generates a translational movement of the tapered element 7g to the left, thus causing the tapered base element 7h to press the tapered element 7g against the cylinder 7a and so block both the translational and the rotational degree of freedom of the cylinder 7a and the engagement member 2.

Once the engagement member 2 has been fixed to the second frame section 4, the force applicator 7 is detached from the head holder by loosening the box nut 7i which engages the tapered base element 7h of the coupling means 6. The pins 10 remain in a corresponding recess in the threaded sleeve 7d or the rotational element 7f.

An alignment aid 17 which extends between the ends of the arms of the L-shaped frame sections 3, 4 can also be detached from the head holder once the first and second frame sections 3, 4 and the second engagement member 2 have been fixed relative to each other.

Figure 2:
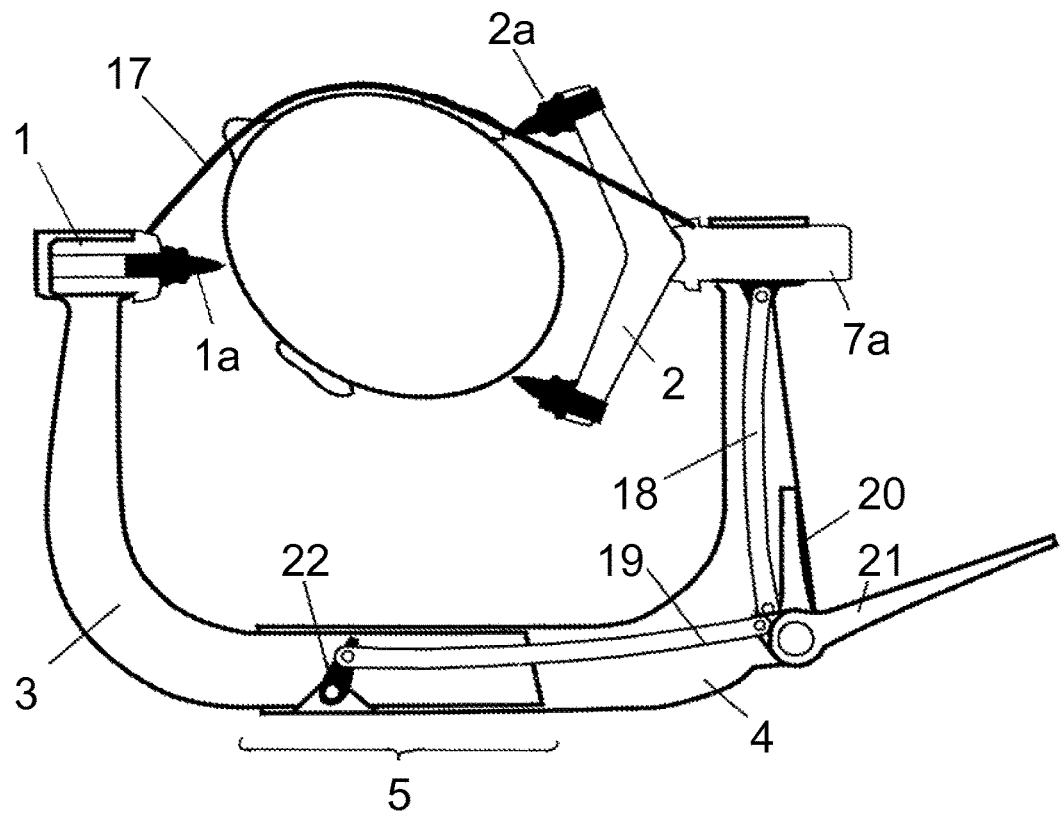
FIG. 2 shows a second embodiment of the head holder in accordance with the invention.

FIG. 2 shows an alternative embodiment of the head holder of the present invention and a patient's head (not provided with a reference sign), wherein the patient's head is engaged by the head pins 1a and 2a of the engagement members 1 and 2 and the force applicator has already been detached from the head holder.

This embodiment consists of a hollow or thin shell construction which allows levers and mechanisms to be integrated internally.

The hollow second frame section 4 encompasses push bars 18 and 19 which are connected to levers 20 and 21, respectively. The push bars 18 and 19 are able to bend, and the levers 20 and 21 are attached to the second frame section 4. The push bar 18 acts on the cylinder 7a coupled to the engagement member 2 and can fix the cylinder 7a to the second frame section 4 in a frictional fit or form fit.

The levers 20 and 21 fit closely with the second frame section 4 in their closed position, such that a securely locked position can be clearly identified, whereas in an unsecured or open position, the lever(s) 20 and/or 21 protrude out of the second frame section 4.

The connecting means 5 comprise an additional lever 22 which has the same function as the lever 16 of the first embodiment shown in FIG. 1.

The levers 20 and 21 differ in size, such that the surgeon can identify the correct lever by touch, without having to look at the levers.

The invention claimed is:

1. A medical head holder, comprising:
   at least two opposing engagement members configured to engage a head of an associated patient, the at least two opposing engagement members comprising a first engagement member and a second engagement member;
   a frame comprising a first frame section and a second frame section, the first and second frame sections being displaceably coupled with each other, the first frame section supporting the first engagement member;
   a connecting member which allows the first and second frame sections to be displaced and which guides the first and second frame sections relative to each other, the connecting member detachably and selectively fixing the first and second frame sections with each other;
   a coupling member which is attached with the second frame section and which displaceably couples the second engagement member with the second frame section and which can be selectively fixed to the second frame section; and
   a force applicator configured to selectively act on the coupling member so as to cause the second engagement member displaceably coupled by the coupling member with the second frame section to be selectively displaced relative to the first engagement member along a displacement direction to hold the head of the associated patient between the first and second engagement members, and to be selectively fixed relative to the second frame section with the head of the associated patient held between the first and second engagement members,
   wherein, with the second engagement member fixed relative to the second frame section via the coupling member, the force applicator is detachable from the second frame section,
   wherein the coupling member maintains, with the force applicator detached from the second frame section, the second engagement member fixed with the second frame section and thereby maintains the head of the associated patient held between the first and second engagement members.

2. The medical head holder according to claim 1, wherein:
   both displacing the first and second frame sections relative to each other and displacing the second engagement member relative to the second frame section alters a distance between the at least two opposing engagement members,
   displacing the first and second frame sections relative to each other effects a coarse adjustment of the distance between the two opposing engagement members; and displacing the second engagement member relative to the second frame section effects a fine adjustment of the distance between the two opposing engagement members.

3. The medical head holder according to claim 1, wherein the second engagement member is free while being displaced to rotate about an axis which is parallel to the displacement direction, and wherein the coupling member is configured to block the second engagement member from rotating once the second engagement member has been displaced a predetermined distance.

4. The medical head holder according claim 1, further comprising a fastener selectively coupling the force applicator with the coupling member carrying the second engagement member.

5. The medical head holder claim 1, wherein the force applicator comprises a gripping member which is configured to be gripped by an associated human user of the medical head holder, the gripping member being operable by the associated human user to either displace or fix the second engagement member.

6. The medical head holder according claim 1, wherein the force applicator comprises a coupling which transmits at least one of a force, a torque, or a force and a torque from the force applicator to the coupling member and which allows the force applicator to be separated from the second frame section.

7. The medical head holder according claim 1, wherein the force applicator comprises a force indicator which indicates a force acting on the head of the associated patient via the at least two opposing engagement members.

8. The medical head holder according claim 1, wherein:
the connecting member comprises a translational guide; and
the first and second frame sections are displaceable relative to each other by the translational guide in a translational movement.

9. The medical head holder according claim 1, wherein the connecting member comprises a form-fit fastener comprising:
a first toothed member which is assigned to the first frame section; and
a second toothed member which is assigned to the second frame section,
wherein the first and second toothed members are operative between a closed relative position to engage each other, thereby preventing a relative movement of the frame sections, and an open position disengaged from each other thereby permitting the relative movement of the frame sections.

10. The medical head holder according claim 9, further comprising:
a resilient coupling operative to couple the second toothed member with the second frame section, the resilient coupling allowing the second toothed member to move relative to the second frame section in a direction perpendicular to a relative movement direction between the first and second frame sections.

11. The medical head holder according claim 10, wherein at least one of the following settings is possible for the resilient coupling:
a fully open setting wherein the first and second toothed members are disposed out of engagement, whereby relative movement of the frame sections possible in both directions;
a half-open setting wherein engagement of the first and second toothed members is caused solely by a resilient force of the resilient coupling acting on one of the first and second toothed members, whereby relative movement of the frame sections possible in one direction only, preferably in a direction which reduces the distance between the two opposing engagement members;
a closed setting wherein engagement of the first and second toothed members is caused by a fixing mechanism, whereby no relative movement of the frame sections possible;
wherein of the form-fit fastener comprises a lever configured to assume different positions in accordance with the different fully open, half-open, and closed settings and wherein the lever is configured to act on the resilient coupling.

12. The medical head holder according claim 1, wherein substantially all of the elements of the head holder are made of one or more of a radiolucent material, a carbon fiber laminate, carbon fiber reinforced PEEK™ polymer, and/or a polyether ketone.

13. The medical head holder according claim 1, wherein substantially all of the radio-opaque elements of the head holder, are configured to be detached from the head holder, specifically once the first and second frame sections and the second engagement member have been fixed relative to each other.

14. The medical head holder according claim 1, further comprising:
an alignment aid extending between the first and second frame sections, the alignment aid being configured to be detached from the head holder after the first and second frame sections and the second engagement member have been fixed relative to each other.

15. The medical head holder according to claim 14, wherein a length of the alignment aid is adjustable or wherein the alignment aid is a flexible strap.

* * * * *